April 12, 1960 E. S. BOERNER Plant Pat. 1,932
CHRYSANTHEMUM PLANT
Filed Aug. 13, 1959
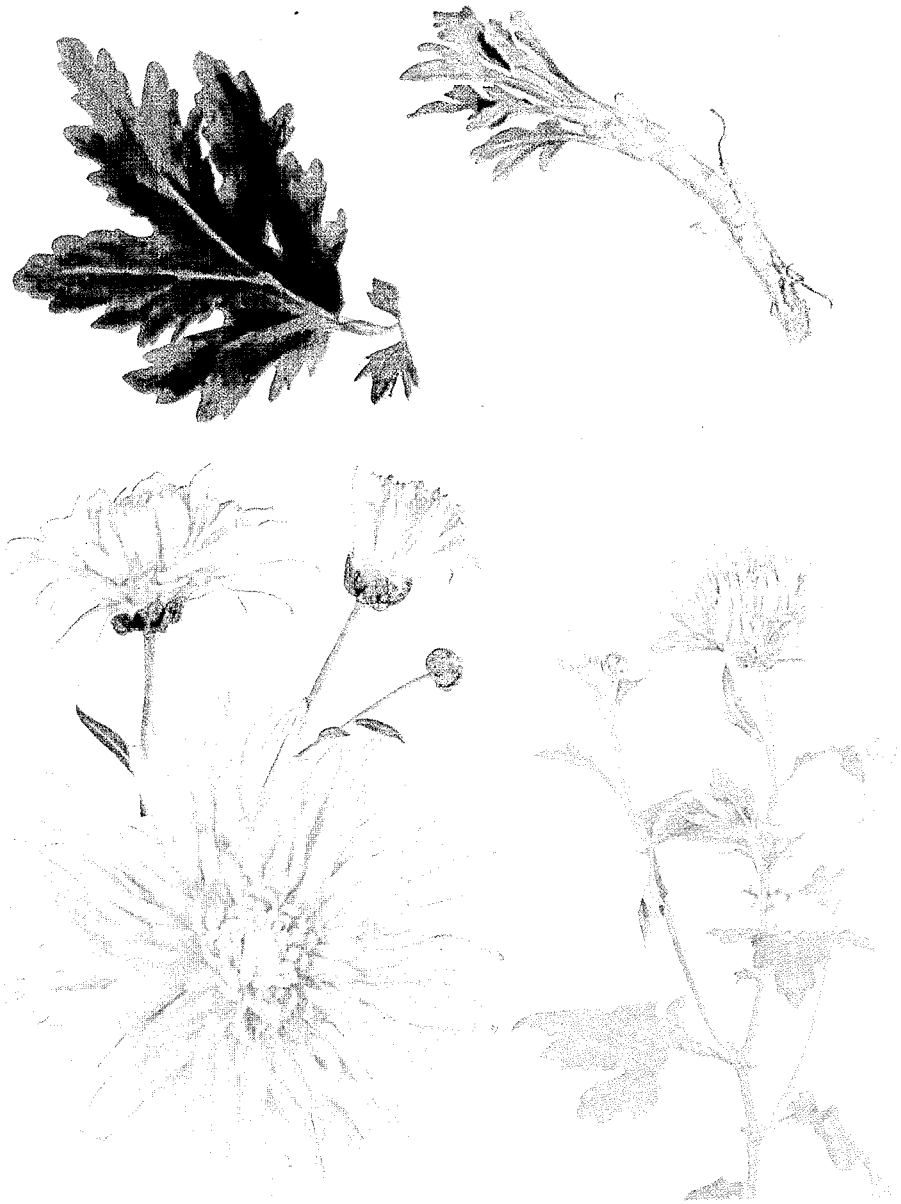
Inventor
E. S. Boerner
By: Robb & Robb
Attorneys.

United States Patent Office

Plant Pat. 1,932
Patented Apr. 12, 1960

1,932

CHRYSANTHEMUM PLANT

Eugene S. Boerner, Newark, N.Y., assignor to Jackson & Perkins Company, Newark, N.Y., a corporation of New York Application August 13, 1959, Serial No. 833,659

1 Claim. (Cl. 47—60)

The present invention relates to a new and distinct variety of chrysanthemum plant of the shaggy, decorative type, which was originated by me by crossing an unnamed and unpatented seedling derived from a cross of "Meadowlark" (Plant Patent No. 1,305)×"Thrush" (Plant Patent No. 1,168) with the variety of "Orchard Oriole" (Plant Patent No. 1,461).

The primary objective of this breeding was to produce a new chrysanthemum variety in which there is combined the large bloom size and early blooming habit of the unnamed seedling parent, with the vigorous plant habit and size of the parent variety "Orchard Oriole." This objective was fully achieved, along with other improvements, as evidenced by the following unique combination of characteristics which are outstanding in the new variety and which distinguish it from its parents as well as from all other varieties of which I am aware:

(1) A vigorous and free habit of growth;
(2) An early blooming habit;
(3) Large bloom size;
(4) Shaggy and decorative flower form; and
(5) A distinctive Carrot Red general color tonality of the flowers, lightly overcast with Scarlet.

Asexual reproduction of my new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character, as well as a typical specimen plant which is depicted in black-and-white, as illustrative of the form and habit of growth of the plant.

The following is a detailed description of the new variety, with color terminology in accordance with Ridgway's Color Standards and Nomenclature, as based upon observations made from specimens grown outdoors at Newark, New York, near mid-morning in the latter part of September:

Parentage: An unnamed seedling of "Meadowlark" ×"Thrush"×"Orchard Oriole."
Classification: Shaggy decorative.
Growth: Very free.
Cold resistance: Hardy.
Blooming period: In the Newark, New York climatic area, the plants bloom from about September 20 until frost.

*Flower*

Bud:
*Color.*—When sepals first divide—Coral Red, Plate 13. When petals begin to unfurl—Scarlet, Plate 1, lightly overcast with Nopal Red, Plate 1. When half blown: inside of petals—Jasper Red, Plate 13, lightly overcast with Scarlet-Red, Plate 1. Outside of petals—Scarlet, Plate 1, very lightly overcast with Scarlet Red, Plate 1.
*Peduncle.* — Color — Biscay Green, Plate 17. Strength—strong.

Bloom:
*Size.*—About 5½ inches.
*Stem.*—Strong.
*Form.*—Decorative.
*Petalage.*—Double.
*Color.*—Center of flower—Salmon-Orange, Plate 2. Outer petals—Carrot Red, Plate 14. Base of petals—Light Green Yellow, Plate 6. Inside of petals—Carrot Red, Plate 14, lightly overcast with Scarlet, Plate 1. Reverse of petals—Strawberry Pink, Plate 1.
*Petals.*—Texture—thick. Form—long.
*Fragrance.*—Characteristic chrysanthemum.

*Plant*

Form: Medium height.
Growth: Vigorous; free.
Foliage:
*Size.*—Large.
*Quantity.*—Normal.
*Color.*—Upper side—Deep Dull Yellow-Green (2), Plate 32. Under side—Bice Green, Plate 17.
*Texture.*—Leathery.

I claim:

A new and distinct variety of chrysanthemum plant of the shaggy decorative type, substantially as herein shown and described, characterized particularly as to novelty by the unique combination of a vigorous and free habit of growth, an early blooming habit, large size of the blooms, a shaggy and decorative flower form, and a distinctive Carrot Red general color tonality of the flowers, lightly overcast with Scarlet.

No references cited.